United States Patent [19]

Wong

[11] Patent Number: 4,743,247
[45] Date of Patent: May 10, 1988

[54] PROCESS FOR MANUFACTURING DOSAGE FORM

[75] Inventor: Patrick S. Wong, Hayward, Calif.

[73] Assignee: ALZA Corporation, Palo Alto, Calif.

[21] Appl. No.: 846,403

[22] Filed: Mar. 31, 1986

Related U.S. Application Data

[63] Continuation of Ser. No. 639,982, Aug. 13, 1984, abandoned.

[51] Int. Cl.$^4$ ............................................. A61K 9/22
[52] U.S. Cl. ................................. 604/892.1; 424/468; 424/472
[58] Field of Search ............... 424/DIG. 7, 16, 19, 424/21, 38, 468, 472; 604/890–892

[56] References Cited

U.S. PATENT DOCUMENTS

| | | | |
|---|---|---|---|
| 3,975,350 | 8/1976 | Hudgin et al. | 128/334 R |
| 4,111,202 | 9/1978 | Theeuwes | 424/19 |
| 4,111,203 | 9/1978 | Theeuwes | 424/19 |
| 4,160,020 | 7/1979 | Ayer et al. | 424/19 |
| 4,235,236 | 11/1980 | Theeuwes | 604/892 |
| 4,298,003 | 11/1981 | Theeuwes et al. | 604/892 |
| 4,320,759 | 3/1982 | Theeuwes | 604/892 |
| 4,361,545 | 11/1982 | Powell et al. | 424/19 |
| 4,434,153 | 2/1984 | Urquhart et al. | 604/892 |
| 4,449,983 | 5/1984 | Cortese et al. | 604/892 |
| 4,450,150 | 5/1984 | Sidman | 604/891 |
| 4,484,921 | 11/1984 | Swanson et al. | 424/19 |

*Primary Examiner*—John F. Niebling
*Assistant Examiner*—Nan X. Nguyen
*Attorney, Agent, or Firm*—Paul L. Sabatine; Edward L. Mandell; Shelley G. Precivale

[57] ABSTRACT

A device is disclosed with an internal space for receiving a beneficial agent. The device comprises a wall surrounding a compartment provided with an internal space and a hydrogel. A passageway in the wall connects the exterior of the device with the internal space. The passageway is used for filling the space with a beneficial agent, and then for dispensing the beneficial agent from the device.

4 Claims, 1 Drawing Sheet

PROCESS FOR MANUFACTURING DOSAGE FORM

CROSS-REFERENCE TO RELEATED APPLICATION

This application is a continuation of Ser. No. 06/639,982 filed Aug. 13, 1984 now abandoned.

FIELD OF THE INVENTION

This invention pertains to an osmotic dispensing device. More particularly, the invention relates to an osmotic dispensing device comprising a compartment provided with an agent receiving space. The invention also concerns a process for manufacturing the dispensing device.

BACKGROUND OF THE INVENTION

Osmotic devices for delivering a beneficial agent to environments of use are known to the prior art in U.S. Pat. No. 3,845,770 issued to Theeuwes and Higuchi, and in U.S. Pat. No. 3,916,899 issued to the same patentees. The osmotic devices disclosed in these patents comprise a semipermeable wall that surrounds a compartment containing a beneficial agent. The semipermeable wall is permeable to the passage of an external fluid, and it is substantially impermeable to the passage of agents. A passageway is provided through the wall for delivering the beneficial agent from the device. These prior art devices release the beneficial agent by imbibing fluid through the semipermeable wall into the compartment in a tendency towards osmotic equilibrium, at a rate determined by the permeability of the wall and the osmotic pressure gradient across the wall, to form in the device an aqueous solution containing the beneficial agent that is dispensed through the passageway from the device. These devices are extraordinarly effective for delivering an agent that is soluble in the fluid and exhibits an osmotic pressure gradient across the semipermeable wall against the external fluid, and for delivering an agent that has limited solubility in the fluid and is admixed with an osmotically effective compound that is soluble in the fluid and exhibits an osmotic pressure gradient across the semipermeable wall against the fluid. The beneficial agent is incorporated into these devices during manufacture, prior to forming the semipermeable wall around the compartment.

The prior art devices operate successfully for delivering a wide variety of aqueous-soluble beneficial agents to an environment of use. The devices also are successful for delivering numerous difficult to deliver agents to an environment of use. Prior to this invention, as noted immediately above, the devices were filled with a beneficial agent at the time of manufacture. Now it has been discovered the use of these devices can be enhanced by providing a device that can be filled with the agent at the time of use. For beneficial agents that are sensitive to fluids and light, and for agents that are subject to degradation and possess a short shelf life and, therefore, do not readily lend themselves to previous manufacture, this invention provides a device that can be filled with an agent at the time of use. The devices of this invention can be filled by the hospital pharmacists, the nurse, the physician, or by the veterinarian at the time of use and need for dispensing the beneficial agent to the recipient.

OBJECTS OF THE INVENTION

It is, accordingly, an immediate object of this invention to provide an osmotic dispensing device for the controlled delivery of a beneficial agent, and which device represents an improvement and an advancement in the agent delivery arts.

Another object of the invention is to provide an osmotic dispensing device comprising a compartment with a space that can be filled with a useful agent at the time of use for delivering the agent to a recipient.

Another object of the invention is to provide an osmotic dispensing device comprising an internal space that can be filled at the time of use with an agent that is insoluble to very soluble in an aqueous fluid, and which agent can be delivered by the device at a controlled rate over time.

Another object of the invention is to provide an osmotic dispensing device comprising a compartment containing an area for receiving a beneficial agent and an area containing an expandable driving member consisting of a hydrogel which operates to diminish the area occupied by the beneficial agent thereby delivering the agent from the device at the time of use.

Another object of the invention is to provide an osmotic device comprising a wax and a hydrogel.

Another object of the invention is to provide a process for manufacturing an osmotic dispensing device comprising a compartment with an empty space and a hydrogel.

Other objects, features, aspects and advantages of the invention will be more apparent to those versed in the dispensing art from the following detailed specification taken in conjunction with the figures and the accompanying claims.

BRIEF DESCRIPTION OF THE DRAWINGS

In the drawings, which are not drawn to scale, but are set forth to illustrate various embodiments of the invention, the drawing figures are as follows.

In the drawings and in the specification like parts in related figures are identified by like parts. The terms appearing earlier in the specification and in the description of the drawing figures, as well as embodiments thereof, are further detailed elsewhere in the disclosure.

DETAILED DESCRIPTION OF THE DRAWINGS

Figure 1:
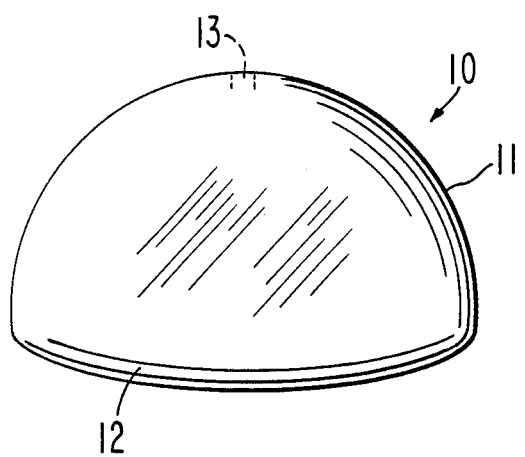
FIG. 1 is a view of an osmotic dispensing device designed for orally administering a beneficial agent to the gastrointestinal tract.

Turning now to the drawings in detail, which are an example of an osmotic dispensing device provided by the invention, and which drawing figures are not to be construed as limiting, one example of the osmotic dispensing device is seen in drawing FIGS. 1 through 4. In FIG. 1, osmotic dispensing device 10 is seen comprising a body member 11 having a wall 12 that surrounds and forms an internal compartment, not seen in FIG. 1. Dispensing device 10 is provided with a passageway 13 in wall 12, which passageway 13 connects the exterior of device 10 with the interior of device 10.

Figure 2:
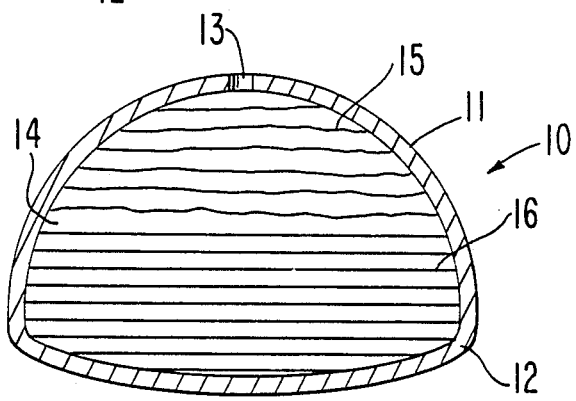
FIG. 2 is an opened view of the osmotic dispensing device of FIG. 1, with FIG. 2 illustrating the internal and the external structure of the dispensing device.

In FIG. 2, dispensing device 10 is seen in opened section. In FIG. 2, device 10 comprises body 11, wall 12, passageway 13 and compartment 14. Wall 12 is formed of a polymeric composition that in at least a part is permeable to the passage of an external fluid and it is substantially impermeable to the passage of a beneficial agent. The polymeric composition forming wall 12 is non-toxic and it maintains its physical and chemical integrity during the dispensing life of device 10.

Internal compartment 14 comprises a first layer 15, identified by wavy lines, adjacent to passageway 13. Layer 15 is formed of a wax that is a solid at ambient temperature and, on being subjected to moderately elevated temperatures, it becomes a low viscosity liquid. By inverting device 10 such that passageway 13 is faced down, the liquid can be poured from device 10 through passageway 13, thereby forming a space inside compartment 14 for receiving a beneficial agent. Compartment 14 further houses a second layer 16 positioned initially distant from passageway 13. Layer 16, identified by straight lines, is formed of an expandable hydrogel. The hydrogel comprising layer 16 is a hydrophilic polymer, that is optionally cross-linked, and it possesses osmotic properties. The osmotic properties of the hydrogel include the ability to imbibe an external aqueous fluid through wall 12, and exhibit an osmotic pressure gradient across wall 12 against the external fluid. Hydrogel layer 16 absorbs fluid imbibed into compartment 14 and swells or expands to an equilibrium state. At equilibrium that osmotic pressure of the hydrogel approximately equals the swelling pressure of the hydrogel, and the osmotic pressure of the hydrogel network is the driving force of the swelling, expanding member. When device 10 is in operation in a fluid environment of use, such as the gastrointestinal tract, hydrogel layer 16 is in contact with a bneficial agent that is subsequently added to compartment 14, layer 16 expands towards passageway 13 and urges such an agent from compartment 14 through passageway 13 from device 10.

Figure 3:
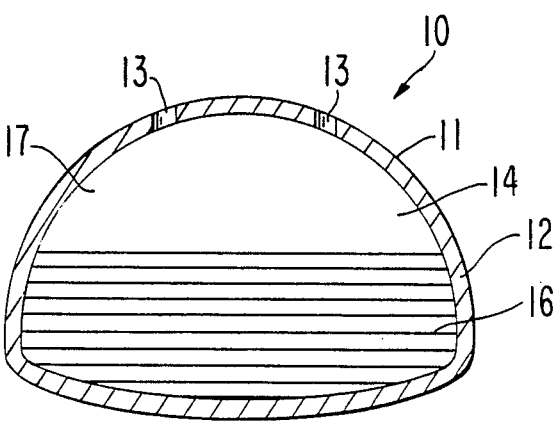
FIG. 3 is an opened view of the osmotic dispensing device provided with a beneficial agent receiving area and a hydrogel driving member for delivering a later received beneficial agent from the dispensing device; and, FIG. 4, is an opened view of a device filled after manufacture of the device.

FIG. 3 illustrates dispensing device 10 in a final manufacture prior to being filled with a beneficial agent. Dispensing device 10 of FIG. 3 comprises body 11, semipermeable wall 12, formed with two passageways 13 and compartment 14. The device is illustrated with two passageways; it should be understood, however, the device can be made with at least one passageway, and it can be made with many passageways. One present advantage of two passageways is air can escape during filling of the device. Compartment 14 comprises a space 17 immediately adjacent to passageway 13 and a hydrogel layer 16. Device 10 is made by first inverting device 10 containing a layer of wax, such that passageway 13 faces down, followed by placing device 10 in a warmed environment such as an oven, or a stream of hot air. In this position and environment, device 10 containing layer 15 formed of a heat-sensitive, heat-responsive meltable wax, melts and flows freely from device 10. As the melting wax drains from device 10 through passageway 13 it concomitantly creates space 17 in compartment 14. Space 17 can be charged with a beneficial agent when needed at the time of use. The present invention thus proves a dispening device that can be filled with an active-beneficial agent after manufacture.

Figure 4:
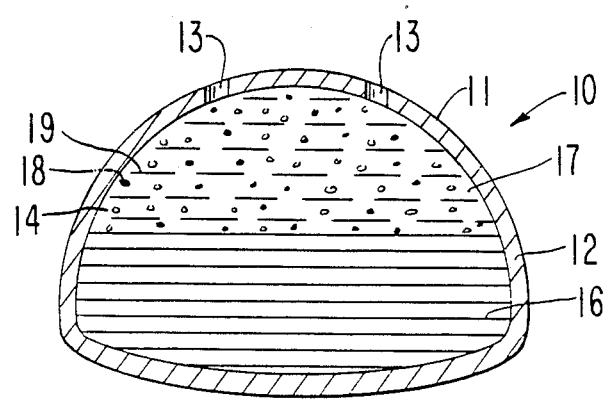

FIG. 4 illustrates dispensing device 10 that is filled with a beneficial agent at a predetermined time. Device 10 is filled with a beneficial agent by inserting a means for filling space 17 through passageway 13 and then charging the beneficial agent into space 17. FIG. 4 depicts device 10 after filling space 17 in compartment 14. In space 17, device 10 contains a beneficial agent formulation 18, represented by dots, which beneficial agent can be from insoluble to very soluble in an aqueous type fluid 19 identified by dashes. The agent formulation 18 exhibits an osmotic pressure gradient across wall 12 against an external fluid that is imbibed into compartment 14. When the beneficial agent has limited solubility in the external fluid it can be mixed with an osmagent that is soluble in the external fluid and exhibits an osmotic pressure gradient across wall 12 against the external fluid. In operation, device 10 containing agent formulation 18 releases said agent by fluid being imbibed into compartment 14 in a tendency towards osmotic equilibrium at a rate determined by the permeability of wall 12 and the osmotic pressure gradient across wall 12. The imbibed fluid continuously forms a solution containing active agent, or a solution of osmagent containing active agent in suspension, which solution in either instance is released by the combined operations of device 10. These operations include the solution being osmotically delivered through passageway 13 due to the continuous formation of solution in the compartment, and by the hydrogel swelling and increasing in volume and expanding into space 17. These actions by hydrogel layer 16 apply pressure against the solution, and thereby deliver it to the exterior of device 10. The device is preferably used for dispensing suspensions, emulsions, organic media, oil-based compositions, hydraulic fluids, semi-hydrophilic fluids, aqueous slurries, and the like.

FIGS. 1 through 4 depict one presently preferred embodiment of device 10. In this embodiment device 10 is made for oral use, that is for releasing either a locally acting or a systemically acting therapeutic agent in the gastrointestinal tract. The oral system 10 can have various shapes and sizes. In one design, device 10 can be curved, such as round, in the vicinity of passageway 13, to increase draining the melted wax from the device. The device can have a diameter of 3/16 to 8/16 inches, or it can be shaped like a capsule having a range of sizes from triple zero to zero, and from 1 to 8.

While FIGS. 1 through 4 illustrate one dispensing device that can be made according to the invention, it is to be understood device 10 can take a wide variety of shapes, sizes and forms for delivering a beneficial agent to the environment of use. For example, the devices include buccal, implant, artificial gland, cervical, intrauterine, nose, and the like. In these forms device 10 can be adapted for administering a beneficial agent to numerous animals, warm-blooded mammals, humans, avians, and reptiles. The device also can be sized, shaped, structured and adapted for delivering an active agent in streams, aquariums, fields, factories, reservoirs, laboratory facilities, hot houses, transportation means, naval means, military means, hospitals, veterinary clinics, nursing homes, farms, zoos, sickrooms, chemical reactions, and other environments of use.

DETAILED DESCRIPTION OF THE INVENTION

In accordance with the practice of the invention, it has now been found that osmotic delivery device 10 can be manufactured with a wall 12 formed of a material that does not adversely affect the agent 18, which includes drug, an osmagent, an animal, or a host; and it is permeable to the passage of an external aqueous type fluid 17, such as water and bilogical fluids, while remaining essentially impermeable to the passage of agents, including drugs, osmagents, and the like. The selectively, semipermeable materials forming wall 12 are insoluble in fluids, and they are non-erodible, hence, they maintain their physical and chemical integrity during operation in the environment of use.

Typical materials for forming wall 12 include semipermeable polymers known to the art as osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, cellulose acetaldehyde dimethyl acetate, cellulose acetate ethyl carbamate, cellulose acetate methyl carbamate, cellulose acetate succinate, cellulose acetate dimethylaminoacetate, cellulose acetate ethyl carbamate, cellulose acetate chloroacetate, cellulose dipalmate, cellulose dioctanoate, cellulose dicaprylate, cellulose dipentanlate, cellulose acetate valerate, cellulose acetate succinate, cellulose propionate succinate, cellulose acetate p-toluene sulfonate, cellulose acetate butyrate, cross-linked selectively semipermeable polymers formed by the coprecipitation of a polyanion and a polycation as disclosed in U.S. Pat. Nos. 3,173,876; 3,276,586; 3,541,005., 3,541,006; and 3,546,142, semipermeable polymers as disclosed by Loeb and Sourirajan in U.S. Pat. No. 3,133,132, lightly cross-linked polystyrene derivatives, cross-linked poly(sodium styrene sulfonate), poly(vinylbenzyltrimethylammonium chloride), cellulose acetate having a degree of substitution up to 1 and an acetyl content up to 21%, cellulose diacetate having a degree of substitution of 1 to 2 and an acetyl content of 21 to 35%, cellulose triacetate having a degree of substitution of 2 to 3 and an acetyl content of 35 to 44.8%, as disclosed in U.S. Pat. No. 4,160,020. Generally, semipermeable materialls useful for forming wall 12 will have a fluid permeability of $10^{-5}$ to $10^{-1}$ (cc·mil/cm$^2$·hr·atm) expressed per atmosphere of hydrostatic or osmotic pressure difference across semipermeable wall 12 can be used for the intended purpose.

The hydrogel suitable for the purpose of the invention are swellable, hydrophilic polymers. The swellable, hydrophilic polymers are in one preferred embodiment lightly cross-linked, such cross-links being formed by covalent or ionic bond, which interact with water and aqueous biological fluids and swell or expand to some equilibrium state. The hydrogels exhibit the ability to swell in water and retain a significant fraction of water within its structure, and when cross-linked they will not dissolve in the water. The hydrogels can be of plant and animal origin, hydrogels prepared by modifying naturally occurring structures, and synthetic polymer hydrogels. The polymers swell or expand to a very high degree, usually exhibiting a 2 to 50 fold volume increase. Hydrophilic Polymeric materials for the purpose include poly(hydroxyalkyl)-methacrylate), poly(N-vinyl-2-pyrrolidone), anionic and cationic hydrogels, polyelectrolyte complexes, poly(vinyl alcohol) having a low acetate residual and cross-linked with glyoxal, formaldehyde, or glutaraldehyde, methyl cellulose cross-linked with dialdehyde, a mixture of cross-linked agar and carboxymethyl cellulose, a waterinsoluble, water-swellable copolymer produced by forming a dispersion of finely divided copolymer of maleic anhydride with styrene, ethylene, propylene, butylene, or isobutylene cross-linked with from 0.001 to about 0.5 moles of a polyunsaturated cross-linked agent per mole of maleic anhydride in the copolymer, water-swellable polymers of N-vinyl lactams, cross-linked polyethylene oxides, and the like.

Other hydrogels include hydrogels exhibiting a cross-linking of 0.05 to 60%, hydrophilic hydrogels known as Carbopol®15 acidic carboxy polymer, Cyanamer® polyacrylamides, cross-linked water-swellable indene maleic anhydride polymers, Good-rite® polyacrylic acid, polyethylene oxide, starch graft copolymers, Aqua-Keeps® acrylate polymer, diester cross-linked polyglucan, and the like. The hydrogels are known to the prior art in U.S. Pat. No. 3,865,108 issued to Hartop., in U.S. Pat. No. 4,002,173 issued to Manning; in U.S. Pat. No. 4,207,893 issued to Michaels; and in *Handbook of Common Polymers* by Scott and Roff, published by the Chemical Rubber Company, Cleveland, Ohio.

The waxes used for the purpose of this invention are solid at ambient temperature and, on being subjected to moderately elevated temperatures, become a low viscosity liquid. The term ambient denotes the termperature of the environment, usually room temperature of 65° F. to 75° F. (about 18° C. to 25° C.). The expression low viscosity indicates the melted wax offers an insignificant or very little resistance to flow from the device. The waxes used for the present purpose can be of plant, animal, insect, mineral or of synthetic origin. The waxes consist of esters and often, in addition, fatty acids, alcohols and hydrocarbons. The waxes can have a broad range of molecular weights, and they usually melt between 45° C. and 95° C. Representative waxes suitable for the present purpose and the melting temperature include beeswax, 64° C.; candellila, 70° C.; carnauba, 82°–86° C.; Japan wax, 53° C., Douglas-fir bark wax, 75°–80° C.; rice-bean wax, 79°–83° C.; castor wax 85°–88° C.; bayberry, 45°–48° C.; montan wax, 82°–87° C.; paraffin wax amber, 87° C., paraffin wax brown, 87° C., and the like.

The expresson beneficial agent formulation as used herein denotes a beneficial agent neat, and a composition of a beneficial agent and an osmagent. The expressions active agent as used herein includes any beneficial agent or compound that can be delivered from the device to produce a beneficial and useful result. The agent can be insoluble to a very soluble in the exterior fluid. For example, the agent can be very soluble in fluid 19 that enters compartment 14 and function as its own osmotically effective solute, or it can be poorly soluble in the fluid and be mixed with an osmotically effective compound that is soluble in the fluid for delivering an agent from the device. The term active agent includes pesticides, herbicides, germicides, biocides, algicides, rodenticides, fungicides, insecticides, anti-oxidants, plant growth promoters, plant growth inhibitors, preservatives, disinfectants, sterilization agents, catalysts, chemical reactants, fermentation agents, sex sterilants, fertility inhibitors, fertility promoters, air purifiers, micro-organism attenuators, drug and other agents that benefit the environment of use.

In the specification and the accompanying claims, the term agent includes drug, and the term drug includes any physiologically or pharmacologically active substance that produces a local or systemic effect, in animals, including warm-blooded mammals; humans 15 and primates; avians; household, sport and farm animals, laboratory animals; fishes., reptiles and zoo animals. The term physiologically as used herein denotes the administration of a drug to produce normal levels and functions. The term pharmacologically denotes variations in response to amount of drug administered to the host. *Stedman's Medical Dictionary*, 1966, published by Williams and Wilkins, Baltimore, MD. The active drug that can be delivered includes inorganic and organic drugs without limitations, those drugs that act on the central nervous system, depressants, hypnotics, sedatives, psychic energizers, tranquilizers, anticonvulsants, muscle relaxants, 20 anti-parkinson agents, analgesics, anti-inflammatory, local anesethetics, muscle contractants, anti-microbials, anti-malarials, hormonal agents, contraceptives, sympathomimetics, diuretics, anti-parasitics, neo-plastics, hypoglycemics, ophthalmics, electrolytes, diagnostic agents, and cardiovascular drugs.

Exemplary drugs that are very soluble in water and can be delivered by the devices of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproternol sulfate, methamphetamine hydrochloride, phenmetrazine hydrochloride, bethanechol chloride, methacholine chloride, pilocarpine hydrochloride, atropine sulfate, methascopolamine bromide, isopropamide iodide, tridihexethyl chloride, phenformin hydrochloride, methylphenidate hydrochloride, oxprenolol hydrochloride, metoprolol tartrate, cimetidine hydrochloride, and the like.

Exemplary drugs that are poorly soluble in water and that can be delivered by the devices of this invention include diphenidol, meclizine hydrochloride, prochlorperazine maleate, phenoxybenzamine, thiethylperazine maleate, anisindone, diphenadione erythrityl tetranitrate, dizoxin, isofurophate, reserpine, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, esteogenic progestational, corticosteriods, hydrocortisone, hydrocorticosterone acetate, cortisone acetate, triamcinolone, methyltesterone, 17$\beta$-estradiol, ethinyl estradiol, ethinyl estradiol 3-methyl ether, prednisolone, 17$\beta$-hydroxyprogesterone acetate, 19-nor-progesterone, norgestrel, norethindone, norethiderone, progesterone, norgesterone, norethynodrel, and the like.

Examples of other drugs that can be delivered by the osmotic device include aspirin, indomethacin, naproxen, fenoprofen, sulidac, diclofenac, indoprofen, nitroglycerin, propranolol, metoprolol, valproate, oxprenolol, timolol, atenolol, alprenolol, cimetidine, clonidine, imipramine, levodopa, chloropromazine, reserpine, methyldopa, dihydroxyphenylalanine, pivaloyloxyethyl ester of $\alpha$-methyldopa hydrochloride, theophylline, calcium gluconate, ferrous lactate, vincamine, diazepam, phenoxybenzamine, $\alpha$-blocking agents, and the like. The beneficial drugs are known to the art in *Pharmaceutical Sciences*, by Remington 14th Ed., 1979, Published by Mack Publishing Co., Easton, Penna.; *The Drug, The Nurse, The Patient, Including Current Drug Handbook*, 1974–1976, by Faiconer, et al., published by Saunder Company, Philadelphia, Penna.; 2 and *Medicinal Chemistry*, 3rd Ed., Vol. 1 and 2, by Burger, published by Wiley-Interscience, New York.

The drugs can be in various forms, such as uncharged molecules, molecular complexes, pharmacologically acceptable salts such as hydrochlorides, hydrobromides, sulfate, laurylate, palmitate, phosphate, nitrite, borate, acetate, maleate, tartrate, oleate, and salicylate. For acid drugs, salts of metals, amines or organic cations, for example quaternary ammonium can be used. Derivatives of drugs such as esters, ethers and amides can be used. Also, a drug that is water insoluble can be used in a form that is a water soluble derivative thereof to serve as a solute and, on its release from the device, is converted by enzymes, hydrolyzed by body pH or other metabolic processes to the original biologically active form. The agent including drug can be present in the compartment with a binder, dispersant, wetting agent, suspending agent, lubricant and dye. Representative of these include suspending agents such as acacia, agar, calcium carrageenan, alginic acid, algin, agarose powder, collagen, colloidal magnesium silicate, colloidal silicon dioxide, hydroxyethyl cellulose, pectin, gelatin and calcium silicate; binders like polyvinyl pyrrolidone and magnesium stearate; wetting agents such as fatty amines, fatty quaternary ammonium salts, and the like. The phrase drug formulation indicates the drug is present in the compartment accompanied by an osmagent, a binder, dye, or the like.

The amount of agent present in the device is initially in excess of the amount that can be dissolved in the fluid that enters the device. Under this physical state, when the agent is in excess, the device will osmotically operate to give a substantially constant rate of release. Generally the device can house from 0.05 ng to 5 g or more, with individual devices containing, for example, 25 ng, 1 mg, 5 mg, 125 mg, 250 mg, 500 mg, 750 mg, 1.5 g, and the like. The devices can be administered once, twice or thrice daily.

The osmagent present in the device, when used according to the mode of the invention, are osmotically effective compounds soluble in fluid that enter the device and exhibit an osmotic pressure gradient across the semipermeable wall against the exterior fluid. Osmotically effective osmagents useful for the present purpose include magnesium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glycose, mixtures thereof, and the like. The osmagent is usually present in an excess amount, and it can be in any physical forms, such as particle, powder, granule, and the like. The osmotic pressure in atmospheres, ATM, of the osmagents suitable for the invention will be greater than zero ATM, generally from zero ATM up to 500 ATM, or higher.

The solubility of an agent in the fluid that enters the compartment can be determined by known techniques. One method consists of preparing a saturated solution comprising the fluid plus the agent as ascertained by analyzing the amount of agent present in a definite quantity of the fluid. A simple apparatus for this Purpose consists of a test tube of medium size fastened upright in a water bath maintained at constant temperature and pressure, in which the fluid and agent are placed and stirred by a rotating glass spiral. After a given period of stirring, a weight of the fluid is analyzed and the stirring continued an additional period of time. If the analysis shows no increase of dissolved agent after successive periods of stirring, in the presence of excess solid agent in the fluid, the solution is saturated and the results are taken as the solubility of the product in the fluid. If the agent is soluble, an added osmotically effective compound optionally may not be needed. If the agent has limited solubility in the fluid, then an osmotically effective compound can be incorporated into the device. Numerous other methods are available for the determination of the solubility of an agent in a fluid. Typical methods used for the measurement of solubility are chemical and electrical conductivity. Details of various methods for determining solubilities are described in *United States Public Health Service Bulletin*, No. 67 of the Hygenic Laboratory; *Encyclopedia of Science and Technology*, Vol. 12, Pages 542 to 556, 1971, published by McGraw-Hill, Inc.; and *Encyclopedia Dictionary of Physics*, Vol. 6, pages 547 to 557, 1962, published by Pergamon Press, Inc. For the purpose of the invention the phrase, "agents with degrees of solubility", as used herein indicates agents that are insoluble to very soluble in aqueous and biological fluids. Further for this purpose, an insoluble agent indicates a solubility of less than 25 mg of agent in a ml of fluid; a poorly soluble agent is one that dissolves in the range of about 25 mg to 150 mg of agent per ml of fluid; a soluble agent dissolves about 150 mg to 600 mg of agent per ml of fluid; and a very soluble agent dissolves in excess of 600 mg of agent per ml of fluid. While the presently preferred embodiments have been described with reference to poorly or very soluble agents, it is to be understood the device can be used to deliver other agents.

The device of the invention is manufactured by standard techniques. For example, in one embodiment the agent and other ingredients that may be housed in one area of the compartment adjacent to the passageway, are pressed into a solid possessing dimension that corresponds to the internal dimensions of the area of the compartment the agent will occupy, or the wax and other ingredients and a solvent are mixed into a solid or semisolid form by conventional methods such as ball-milling, calendering, stirring or rollmilling, and then pressed into a preselected shape. Next, a layer of a hydrogel is placed on contact with the layer of wax in a like manner, and the two layers surrounded with a semipermeable wall. The layering of wax and hydrogel can be fabricated by conventional two-layer press techniques. The wall can be applied by molding, spraying or dipping the pressed shapes into a wall forming material. Another and presently preferred technique that can be used for applying the wall is the air suspension procedure. This procedure consists in suspending and tumbling the pressed wax and dry hydrogel in a current of air and a wall forming composition until the wall is applied to the wax hydrogel composite. The air suspension procedure is described in U.S. Pat. No. 2,779,241; *J. Am. Pharm. Assoc.*, Vol. 48, pages 451 to 459, 1979, and ibid, Vol. 49, pages 82 to 84, 1960. Other standard manufacturing procedures are described in *Modern Plastics Encyclopedia*, Vol. 46, pages 62 to 70, 1969., and in *Pharmaceutical Sciences*, by Remington, 14th Edition, pages 1626 to 1678, 1970, published by Mack Publishing Company, Easton, Penna.

Exemplary solvents suitable for manufacturing the wall include inorganic and organic solvents that do not adversely harm the wall forming material, and the final device. The solvents broadly include members selected from the group consisting of aqueous solvents, alcohols, ketones, esters, ethers, aliphatic hydrocarbons, halogenated solvents, cycloaliphatic, aromatics, heterocycyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethelene glycol monoethyl acetate, methylene dichloride, ethylene dichloride, propylene dichloride, carbon tetrachloride, mitroethane, mitropropane, tetrachloroethane, ethyl ether, isopropyl ether, cyclohexane, cyclo-octane, benzene toluene, naphtha, 1,4-dioxane, tetrahydrofuran, diglyme, water; and mixtures thereof such as acetone and water, acetone and methanol, acetone and ethyl alcohol, methylene dichloride and methanol, and ethylene dichloride and methanol, and the like.

The expression "passageway" as used herein comprises means and methods suitable for filling and releasing the agent from the system after its manufacture. The expression includes aperture, orifice or bore through wall 12 formed by mechanical procedures, or by eroding an erodible element, such as gelatin plug, in the environment of use. A detailed description of osmotic passageways and the maximum and minimum dimensions for a passageway are disclosed in U.S. Pat. Nos. 3,845,770 and 3,916,899.

The following example illustrates means and methods for carrying out the present invention. The example is merely illustrative and it should not be considered as limiting the scope of the invention, as this example and other equivalents thereof will become more apparent to those versed in the dispensing art in the light of the present disclosure, the drawings and the accompanying claims.

A dispensing device is provided as follows. First, 300 mg of polyacrylamide, sold under the name of Cyanamer ® A-370, a hydrogel of approximately 200,000 mol wt is placed into the 7/16 inch die of a Manesty Press and punched under a pressure head of 1½ tons. Then, 300 mg of ground beeswax is added to the Manesty against the pressed hydrogel. The wax is pressed against the hydrogel to form a laminate comprising a lamina of wax and a lamina of hydrogel.

Next, a semipermeable wall is provided by blending 170 g of cellulose acetate having an acetyl content of 39.8% with 400 ml of methylene chloride and 400 ml of methanol, and spray coating the two layered compartment forming member in an air suspension machine having a 1.8 kg charge until a 7.2 mil thick semipermeable wall surrounds the compartment. Then, the coated device is dried for 72 hrs at 25° C. in a moving current of air, and a 15 mil passageway is laser drilled through the semipermeable wall. The passageway connects the layer of wax with the exterior of the device. The device then is turned upside down, placed inside a 65° C. oven, wherein the wax melts and flows from the device. The device then is allowed to cool to room temperature, 70° F. (21° C.). The device has an internal agent-receiving space that can be filled at any preselected time. For example, the device can be filled with a micronized composition comprising 249 mg of oxprenolol hydrochloride, 10.7 mg of poly(vinyl-Pyrrolidone) and 8 mg of magnesium stearate by feeding the composition through the passageway into the compartment of the device.

The novel osmotic systems of this invention use means for the obtainment of precise release rates in the environment of use while simultaneously maintaining the integrity and character of the system. While there has been described and pointed out features of the invention as applied to presently preferred embodiments, those skilled in the art will appreciate that various modifications, changes, additions and omissions in the system illustrated and described can be made without departing from the spirit of the invention.

What is claimed is:

1. An article of manufacture useful as a dosage form for dispensing a beneficial agent formulation, the article comprising:
   (a) a shaped wall comprising in at least a part a semipermeable composition permeable to the passage of an exterior fluid, the wall surrounding and forming:
   (b) a compartment comprising an internal empty space, a layer of a wax and a layer of a hydrogel; and,
   (c) means in the wall for communicating the exterior of the article of manufacture with the compartment.

2. An article of manufacture useful as a dosage form for dispensing a beneficial agent formulation, the article comprising:
   (a) shaped wall comprising in at least a part a semipermeable composition permeable to the passage of an exterior fluid, the wall surrounding and forming:
   (b) a compartment comprising a layer of wax and a layer of a hydrogel; and,
   (c) means in the wall for communicating the exterior of the article of manufacture with the compartment.

3. A process for manufacturing a dispensing device provided with an internal empty space for receiving beneficial agent formulation, the process comprising:
   (a) forming a layer of wax;
   (b) surrounding the layer of wax with a wall comprising in at least a part a semipermeable composition;
   (c) forming at least one passageway in the wall connecting the exterior with the interior of the device;
   (d) heating the wax; and,
   (e) draining the wax through a passageway from the device, thereby providing an internal empty space in the device.

4. A process for the manufacture of a dosage form provided with an internal space for receiving a beneficial agent formulation, the process comprising:
   (a) forming a layer of a hydrogel;
   (b) forming a layer of wax in contact with the hydrogel;
   (c) surrounding the layers with a wall comprising in at least a part a semipermeable composition;
   (d) forming at least one passageway in the wall connecting the exterior with the interior of the dosage form;
   (e) heating the dosage form to melt the wax; and,
   (f) draining the wax through a passageway from the dosage form to provide an internal empty space in the dosage form.

* * * * *